US007383196B1

(12) United States Patent
Tang et al.

(10) Patent No.: US 7,383,196 B1
(45) Date of Patent: Jun. 3, 2008

(54) METHOD FOR OPERATING ACTIVE CLINICAL GUIDELINES

(75) Inventors: Paul C. Tang, Los Altos, CA (US); Charles Y. Young, Palo Alto, CA (US)

(73) Assignee: Epic Systems Corporation, Madison, WI (US)

( * ) Notice: Subject to any disclaimer, the term of this patent is extended or adjusted under 35 U.S.C. 154(b) by 0 days.

(21) Appl. No.: 09/524,826

(22) Filed: Mar. 14, 2000

(51) Int. Cl.
*G06Q 50/00* (2006.01)
(52) U.S. Cl. ......................................................... 705/3
(58) Field of Classification Search .................... 705/2, 705/3; 600/300; 128/904; 345/760
See application file for complete search history.

(56) References Cited

U.S. PATENT DOCUMENTS

| 5,619,991 | A | * | 4/1997 | Sloane | 600/300 |
| 5,737,539 | A | * | 4/1998 | Edelson et al. | 705/3 |
| 5,758,095 | A | * | 5/1998 | Albaum et al. | 705/2 |
| 5,845,255 | A | * | 12/1998 | Mayaud | 705/3 |
| 5,884,309 | A | * | 3/1999 | Vanechanos, Jr. | 707/10 |
| 5,895,461 | A | * | 4/1999 | De La Huerga et al. | 707/1 |
| 5,903,889 | A | * | 5/1999 | de la Huerga et al. | 707/3 |
| 5,911,132 | A | * | 6/1999 | Sloane | 705/3 |
| 6,018,713 | A | * | 1/2000 | Coli et al. | 705/2 |
| 6,022,315 | A | * | 2/2000 | Iliff | 600/300 |
| 6,067,523 | A | * | 5/2000 | Bair et al. | 705/3 |
| 6,149,585 | A | * | 11/2000 | Gray | 600/300 |
| 6,264,614 | B1 | * | 7/2001 | Albert et al. | 600/528 |
| 6,308,171 | B1 | * | 10/2001 | De La Huerga | 707/3 |
| 6,408,330 | B1 | * | 6/2002 | DeLaHuerga | 709/217 |
| 6,421,650 | B1 | * | 7/2002 | Goetz et al. | 705/3 |

OTHER PUBLICATIONS

"Off the Charts an Electronic Medical Records System at the University of Illinois Medical Center . . . Technology Believers", Koch, Christopher,Feb. 1, 2003, CIO, pp. 46-50, Dialog File 15, Acc. 02538012.*
Preston Gralla, How The Internet Works, Aug. 1999, Que, Millennium Edition, pp. 145-157, 166-169.*

* cited by examiner

*Primary Examiner*—C Luke Gilligan
*Assistant Examiner*—Russell Shay Glass
(74) *Attorney, Agent, or Firm*—Quarles & Brady LLP

(57) ABSTRACT

An active guidelines capability or component is linked to a computerized patient record system to integrate the use of clinical guidelines in the workflow of clinicians treating patients. Many healthcare institutions maintain sets of clinical guidelines describing recommended treatment or analysis options for patients displaying sets of symptoms or for whom certain diagnoses have been made. The active guidelines feature adds an active guidelines tag to such clinical guidelines so that when the clinician accesses the clinical guidelines and wishes to follow the recommendation, the clinician merely has to click on a hypertext created from the tag which then transmits action orders, also contained in the tag, to be transmitted to the computerized patient record system for implementation.

12 Claims, 1 Drawing Sheet

METHOD FOR OPERATING ACTIVE CLINICAL GUIDELINES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

When patients are seen, treated, or tested by medical practitioners and technicians, the events of the interaction are recorded by the medical professionals. Those recordings become part of the medical records of the patient. The maintenance of these medical records for a patient are a essential part of modern medical treatment of the patient. Recently, the technology of recording and archiving medical records has undergone a dramatic evolution. Instead of the previous bulky paper recording systems, modern medical and health care institutions are adopting electronic medical records systems, sometimes also known as computerized patient records systems. Such computerized record keeping systems offer significant advantages to the practitioners and to the patient, as well as to the health care institution as a whole.

Electronic medical records systems are typically accessible by clinical service providers from throughout the health care institution, without the need for tracking down a particular paper file. Electronic medical records make it easier to track orders and results and to ensure that orders and results are flagged for the attention of the appropriate health care professional. Electronic medical records provide a centralized depository of the health care records of the patient, thus making it easier for all professionals seeing the patient to be aware of particular medical conditions, and avoiding the need to transfer paper files around the institution. From the viewpoint of the health care institution, electronic capture and analysis of patient visit, diagnosis, treatment and results information make possible the realistic evaluation of clinical outcomes in view of any desired input parameter. Thus the use of electronic medical records continues to rapidly grow.

Many medical and health care institutions also maintain a set of clinical practice guidelines for the benefit of health care providers. Such clinical guidelines are not intended to prevent a practitioner from exercising the necessary judgment in treating a particular patient, but are intended to provide a common framework throughout the institution for the diagnosis and treatment of common medical problems in a relatively consistent manner. For example, a pediatric practice might have a clinical guideline for the evaluation, initial treatment, and then for the escalation of treatment if unsuccessful, for childhood earaches. Such protocols are recorded in a form accessible throughout the institution so that the health care providers can refer to those guidelines in making actual decisions on patient care. In the past, such clinical guidelines were often distributed in booklet or written form, and now they are often made available by computerized access.

While the use of clinical guidelines sounds in theory to be a very practical idea, the manner in which such guidelines are implemented often leaves the guidelines out of the normal workflow of the clinical service providers. All of the health care workers in an institutions, including physicians, nurses, technicians and aides and assistants, are typically very busy and their time is often tightly scheduled. Therefore, while taking time to refer to a published set of clinical guidelines does not in theory sound like a great burden, in the life of a busy clinician seeing patients, if a referral to the clinical guidelines is not convenient to make in the normal workflow for the clinician, the reference to the clinical guidelines may not be made.

This is true even in environments in which all the information is in electronic form. For example, like other institutions, health care institutions often now maintain an intranet in which information is posted for access around the institution in electronic form. In such an intranet, the users of the systems typically use a form of a web browser program, such as Netscape Navigator or Microsoft Internet Explorer, to navigate around and find information in the institution's intranet. However, when those same clinicians are updating the medical records for a patient, those users are typically not using the web browser program of the institution, but are typically using the electronic medical records system software for the institution. Typically, the only way available to transfer information from the clinical guidelines into a medical record is to physically transcribe the information for later entry into the medical records system. In part, this is because of the format of typical intranet (or internet) web pages, which are generally composed in HTML or (in the future) XML syntax, while the medical records systems use their own unique forms of data structure and information formatting.

Accordingly, what is needed is a method to more easily integrate an institution's clinical guidelines into the normal workflow for the clinicians actually charting the patients medical records.

BRIEF SUMMARY OF THE INVENTION

The present invention is summarized in that the active guidelines for a health care institution are published in a web format, such as HTML or XML, but also have incorporated into the documents containing the guidelines a set of active guideline tags specifying actions to be taken in an electronic medical records system. The active guideline tags are presented in the display to the user in the same format used to present a universal resource locator (URL) address, i.e. appearing like a typical hyperlink to a web page. The clinician when viewing the active clinical guidelines can then activate the action items by invoking the hyperlink as it appears on his or her computer screen. The active guideline tag underlying the hyperlink is then transmitted to the electronic medical records system, both for incorporation into the patients medical record and to initiate the requested action.

The medical records system thus constructed is intended to place the ability to use practice guidelines in the everyday creation of medical records. The clinician can, with little more than the click of a computer mouse, import action items derived from the active guidelines web pages which are then transferred as a whole into action items in the electronic medical records system. Thus not only are the practice guidelines incorporated into the everyday work flow, but the use of the protocol or treatment plan suggested in the clinical guidelines become easier to do than doing something else, thus encouraging utilization of the guidelines themselves.

It is an advantage of the present invention that it permits the active guidelines to be viewed by web browsers not imbedded in medical records systems without the users being aware that there is anything that they are not seeing.

Other objects, advantages and features of the present invention will become apparent from the following specification when taken in conjunction with the accompanying drawings.

DETAILED DESCRIPTION OF THE INVENTION

Figure 1:
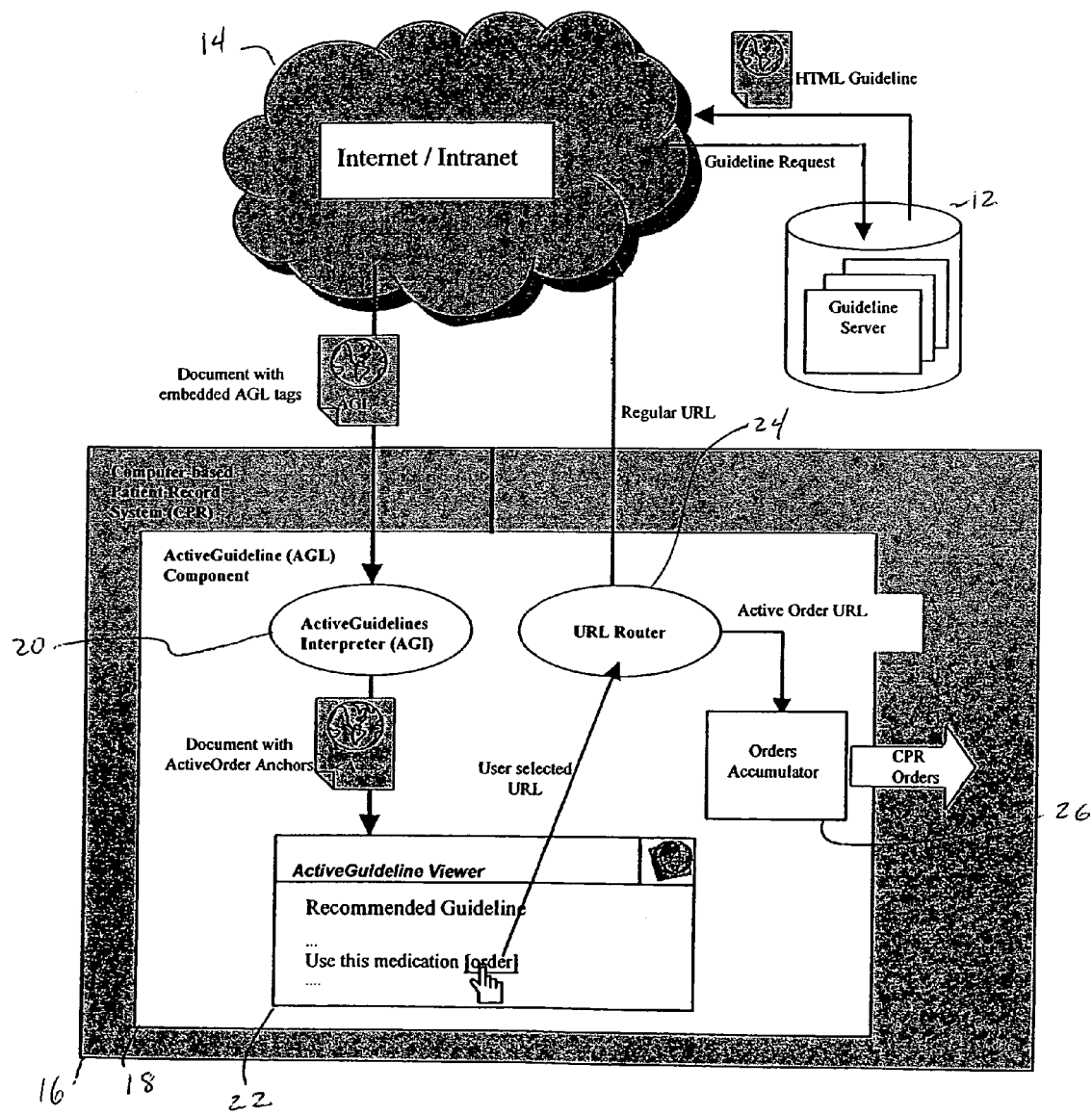
FIG. 1 is a schematic illustration of the logic of data flow for an embodiment of the present invention.

The idea of this invention is to integrate the use of clinical guidelines at a health care institution into the use of an electronic medical records system. To accomplish that objective, the clinical guidelines are made "active," meaning that the guidelines have imbedded in them active commands that can be interpreted by an electronic medical records software system. It is preferred that the guidelines be displayed in the form of an otherwise normal appearing web page, whether on an intranet or through internet access. The web page containing the clinical guidelines contains within it an active guideline tag containing series of active instructions that can be interpreted by an electronic medical records system. When the user of the system is in the process of charting for the patient, the clinician can actually implement various kinds of orders, for example for lab tests or to prescribe drugs, by simply accepting and thus implementing, the action recommendation contained in the tag associated with the clinical guideline appropriate for that patient.

The conventional practice at larger health care institutions or departments of such institutions today is to post the clinical guidelines on a web page accessible by computer network from anywhere in the institution, or at least anywhere in the department. The web pages is therefore typically a document composed in HTML format, although the use of other formats, and in particular the use of XML format, is specifically envisioned. The electronic medical records system should have embedded in it a web browser capability. The difference in an active guidelines architecture is that the guideline document also includes a special coding for initiating action items in the medical records system included with each guideline. The action item coding is interpreted by an active guideline interpreter which presents an image or text to the user with an associated URL pointer. It is a feature of this approach that it can be implemented in a manner that conventional browser programs, i.e. ones without the active guidelines capabilities, can still view the guidelines as web documents without any awareness that any capabilities are unavailable to such viewers.

It is envisioned that this invention is to be used with an electronic medical records systems, also known as a computerized patient records system, terms which are used here synonymously. The medical record system should also have order processing or prescription generation capabilities, although some in the field package these capabilities as separate products. This description also refers to web browsers, which is the common name in the industry for software capable of interpreting and presenting to the user information stored in HTML or XML format, typically through a TCP/IP interface. Since this invention is implemented mainly in computer software, it is intended that the illustrations and examples presented here be interpreted as exemplary of the underlying logic rather than as physical representations of the operation of a system embodying this invention.

The conceptual schematic of FIG. 1 is intended to help explain the working of this embodiment. This embodiment is one intended to fit within the architecture of the EpicCare medical records system from Epic Systems Corporation. EpicCare has embedded within it a web browser software module, which gives the user web browsing and HTML interpretation capabilities while still in the EpicCare system. In this embodiment, the clinical guidelines of the institution reside on a guideline server indicated at 12. The guideline server 12 is simply a computer or processor with a storage device having the information representing the clinical guidelines stored therein. The guidelines are prepared and stored in the format of web pages, e.g. in HTML or XML format, with additional information attached to each guideline, as will be discussed further below. Communications between the user and the guidelines server can be through either an institutional intranet or through conventional internet connection, indicated at 14. At the work station of the user of the system, a computer or processor based system is operating a computerized medical records system, indicated by the block at 16. This logical block could, for example be the EpicCare computerized patient records system. Within the logical block 16 is another logical block labeled 18, representing the active guideline component of the system. The nested depiction of the blocks 16 and 18 is not intended to represent physical reality, but is intended to represent that the active guideline component is a function operating within, or called by, the computer-based patient record system. Within the active guideline component 18 is an active guideline interpreter 20, an active guideline viewer 22, and a URL router 24. The active guideline interpreter 20 is software which functions to parse the clinical guideline information and tags received from the guideline server 12 to convert the embedded guideline tags in the guideline document into a set of hyperlinks containing uniform resource locators (URLs). The active guidelines are then displayed by the active guideline viewer 22 on a display device accessible to the user in a format similar to common HTML web page documents.

There is one important difference, however, in how the active guidelines are displayed by the active guideline viewer 22, as compared to how the same guideline would be displayed by a conventional web browser not equipped for active guidelines. This difference might best be illustrated by a simplistic example. Consider a situation in which the clinical guideline is to recommend to the patient that he or she take two aspirin tablets each morning. In the conventional browser view, the user browsing the guidelines sees just the medical action suggested itself, i.e.:

TAKE TWO ASPIRIN DAILY

In the browser view using the active guideline interpreter and viewer, the user see the same recommendation to direct the patient to take two aspirins, but in addition is presented with a hypertext link, here labeled "[ORDER]":

TAKE TWO ASPIRIN DAILY [ORDER]

The word "Order" in brackets appear above to represent a word or phrase presented to the used appearing as a hypertext link in the browser. The hyperlink word of phrase could be the actual word "order" or "accept" to indicate acceptance of the clinical guidelines or could be a word or phrase describing the action to be take, i.e. "Recommend two aspirin." If the clinician intends to follow the recommendation in the clinical guideline, that clinician merely needs to invoke the hypertext link, typically by clicking on the hypertext words with the computer mouse. This gives the user of the system the ability to simply click on the hypertext link to "order" to initiate a series of action orders which are transmitted to the electronic medical records system to electronically commence the action sequence recommended in the clinical guidelines, in this case to recommend the taking of two aspirin daily. The information is also entered into the patients medical record. This is why the term "active guidelines" is used, since this gives the user of the system the ability not only to view the clinical guidelines of the institution but also, by the click of a single mouse stroke, to initiate the recommended procedure.

At a systems level, when the user clicks on the hyperlink "[order]", the active guideline viewer 22, which is again essentially a web browser, transmits the URL address which underlies the [order] hypertext on which the user has clicked. That URL is passed to the URL router 24, which has been programmed to pass on non-active guidelines URL web browsing requests out to the intranet or internet, but which intercepts URL requests that represent active guideline tags that are to be routed to the patient records system. The active guideline tags thus intercepted are interpreted back, to recover the actual medical records instructions and information associated with the clinical guidelines, and those instructions are accumulated (logically if not physically) in an order accumulator. The accumulated orders are transferred periodically, or upon user action, to the electronic medical records system to both update the patient's chart and to create electronic orders to initiate the actions actually requested by the user.

Another way to look at this system is to consider what information resides or is transmitted at each stage of the use of this system. In the active guideline server 12, the clinical guidelines themselves are stored as text in storage associated with the server. The text of the guidelines includes information about actions or orders which are recommended based on certain diagnoses or conditions of the patients. The guidelines can include both action items, such as prescriptions, diagnostic tests, or various other forms of therapeutic treatments as well as text to be inserted into the patients medical records. Associated with each clinical guideline in the server is an embedded active guideline tag. Such tags contain information which would need to be transferred to the computerized patient record system in the event that the user elects to follow a recommendation in the clinical guideline. The tag can therefore be a series of computer codes, text, data or instructions of whatever kind, or a combination of these elements, which can be recognized or processed by the computerized patient record system.

In normal web browsing, when the user requests to view a particular clinical guideline, the user does so by clicking on a hyperlink displayed on the user's display. Clicking on a hyperlink causes the web browser, in this case the active guidelines viewer, to generate a request to retrieve the HTML page associated with the underlying URL in the hyperlink. That request is sent through the intranet or internet to the active guideline server 12. The active guideline server 12 accesses the data storage associated with that request and transmits to the user the text of the selected clinical guideline with the embedded active guideline tags. The active guideline and associated tags are received by the active guideline interpreter 20, which interprets the information so as to present to the viewer (and the user) the text of the guideline itself, as well as an acceptance indicator specified by the tags. The acceptance indicator is typically a hyperlink, such as a hyperlink display of a word such as "order". The information from the active guideline tag is kept in the hyperlink and made available to the URL router 24 in case the user decides to invoke the recommendation made in the clinical guideline. If the user invokes the recommendation made in the clinical guideline, the URL router 24 takes the embedded information from the hyperlink and places it in the orders accumulator for processing by the patient records system.

To help in illustration of this system, consider another example. For this system to be implemented, the architects of the active guideline system need to develop a syntax for the medical orders which is compatible with patient record systems. So, as an example, if the clinical guideline is to include an order for the medication fluoxetine, the active guideline tag might read:

```
<AGL type="MED" Name="Floxetine HCL Cap 10 MG"
NDC="077-3104-01" DoseStrength="10 mg" Sig="take 1 cap daily
in the morning for two weeks, then take 2 caps daily in the
morning" Dispense="42" Refill="0">Prozac(fluoxetine) </AGL>
```

This exemplary active guideline order includes leading and trailing delimiters to help to identify this tag from other text. This tag also includes all of the information necessary to transmit to a pharmacy system or module all the information necessary to prescribe a medication for the patient. That information can be converted to an order by the patient record system when the prescription is sent to pharmacy. The next to last right carat (>) also precedes and identifies an acceptance indication of the medication that is associated with this embedded tag.

Consider another example, when a procedure is to be ordered. In this case, a format of an active guideline embedded tag might look something like the following:

```
<AGL type ="PROC" Name ="COMPLETE BLOOD COUNT"
CPT="85001" Priority="Routine"> Complete Blood Count (CBC)
</AGL>
```

Again the tag includes leading and trailing delimiters to identify the tag from other information. The tag includes information on the procedure to be performed, including the name of the procedure, its CPT code for correct billing and insurance processing, and a priority rating. Again at the end of the tag, after the last right carat (>) the display name for the procedure recommendation.

In the above examples, the active guideline interpreter changes some text from normal text in a conventional browser to a hyperlink in an active guideline browser. The active guideline tags can also be specified in such a way that a hyperlink is inserted in an active guideline browser. The example below will insert a hyperlink (displayed as "[Accept]") in the display created by the active guideline browser. A regular browser viewing the same page will not display the "[Accept]" text.

```
<AGL type ="PROC" Name ="COMPLETE BLOOD COUNT"
CPT="85001" Priority="Routine" Text="[Accept]" />
```

Images are treated the same way as text. The active guideline interpreter will insert a hyperlink image or convert a normal image into a hyperlink as appropriate.

In the active guideline interpreter, the active guideline tags are received from the guideline server and processed for presentation to the user of the system. This processing, in essence, converts the tag information to a simple hyperlink representation presented to the user while maintaining the details of information in the hyperlink in a non-displayed format. For example, the active guideline tag above for the prescription for fluoxetine might be processed by the active guideline interpreter to create an active guideline hyperlink that might read as follows:

<A HREF=CPR:/agl/Order.asp?Type=MED&Name+Fluoxetine+ HCl+Cap+10+MG&NDC=0777-3104-01&DoseStrength+10 mg&Sig= Take+1+cap+daily+in+the+morning+for+2+weeks, +then+take+2+caps+ daily+in+the+morning&Dispense=42&refill=0>Prozac (fluoxetine) </A>

This hyperlink will create on the screen of the user a display which reads simply:

Prozac (fluoxetine)

The balance of the information in the hyperlink is not displayed to the user, but is available to be passed to the orders accumulator if the user accepts the clinical guideline recommendation by invoking the hyperlink. The balance of the hidden information in the hyperlink is sufficient to instruct the medications function in the computerized patient records system to create prescription for the recommended medication.

Another way to analyze this system is to consider what tasks each of the elements of the system are to perform. For example, the guideline server is essentially a conventional web server containing the clinical guidelines in its storage device and making the pages stored in its storage device available to any inquiring processor by transmittal over the intranet or the internet. The difference is that for each of the clinical guidelines, the guideline server also includes an association to one or more tags. Each of the tags carries the information to both create a hyperlink in an active guideline capable web browser as well as to convey the medical order, treatment or prescription information to the computerized medical records system.

At the user end, the active guideline component of the electronic medical records system acts like a web browser in presenting the clinical guidelines to the users in a web pages format. The user end processor also converts the tag into the hyperlink also presented to the user in association with the clinical guideline. If the user invokes the recommendation in the clinical guideline by clicking on the hyperlink, the information in the hyperlink is sent to the accumulator for processing by the computerized patient record system.

The result achieved by the active guideline system is that the use of the clinical guidelines at an institution can be integrated into the workflow of the clinicians using the system. In fact, once reference is made to the clinical guidelines, it becomes easier to follow the recommendations contained in the guidelines than doing anything else. The user simply has to click on the hyperlink associated with the guideline to accept the guideline and invoke the actions recommended by the guidelines. This ease of use will tend to foster the use and acceptance of such clinical guidelines across institutions.

We claim:

1. In a computerized patient records system operated for a healthcare institution which maintains written clinical guidelines, a method of operating active guidelines comprising the steps of
   a) on an active guidelines server, maintaining the clinical guidelines and also maintaining, associated with the clinical guidelines, active guideline tags containing information usable by the computerized patient records system to generate orders;
   b) at the station of a user, operating an active guidelines viewer in communication with the guidelines server, the active guidelines viewer including a web browser, an active guidelines interpreter and a URL router,
   i) the active guidelines interpreter receiving the active guidelines tags and converting the active guidelines tags into hyperlinks and passing the hyperlinks to the web browser,
   ii) the web browser receiving and displaying the hyperlink from the active guidelines interpreter for the user representing the active guideline; and
   c) when the user accepts a clinical guideline by invoking a hyperlink, the URL router receiving the active guideline tag associated with the invoked hyperlink and creating an action item from the active guideline tag to be sent to the computerized patient records system for implementation, the action item being processed by the computerized patient record system to create an order.

2. The method of claim 1 wherein the order in step (c) is issuing a prescription.

3. The method of claim 1 wherein the order in step (c) is for a procedure to be performed.

4. The method of claim 1 wherein the station of the user communicates with the active guidelines server over the internet.

5. The method of claim 2 wherein the station of the user communicates with the active guidelines server over the internet.

6. In a multiple server computer system to operate an electronic medical records software system and order entry in a healthcare institution, a method comprising the steps of
   a) providing an active guidelines server, the active guidelines server maintaining a set of clinical guidelines and a set of active guidelines tags, each of the active guidelines tags being associated with at least one of the clinical guidelines and including information usable by the records system to generate orders;
   b) providing a workstation at the location of a clinician, the workstation operating an active guidelines viewer, the active guidelines viewer including a web browser, an active guidelines interpreter and a URL router, the active guidelines interpreter converting the active guidelines tags into a hyperlink with, the web browser displaying for the clinician the hyperlink associated with the clinical guidelines; and
   c) when the clinician chooses a hyperlink presented by the web browser, the URL router receiving the active guideline tag associated with the chosen hyperlink and, if the chosen hyperlink is for an active guidelines order, sending a communication to the electronic medical records software system to cause an order to be entered.

7. The method of claim 6 wherein the order in step (c) is issuing a prescription.

8. The method of claim 6 wherein the order in step (c) is for a procedure to be performed.

9. In a multiple server computer system to operate an electronic medical records software system and order entry in a healthcare institution, a method comprising the steps of
   a) providing an active guidelines server, the active guidelines server maintaining a set of clinical guidelines and a set of active guidelines tags, each of the active guidelines tags being associated with at least one of the clinical guidelines and including information usable by an electronic medical records system to generate orders;
   b) providing a workstation at the location of a clinician, the workstation operating an active guidelines viewer, the active guidelines viewer including a web browser, an active guidelines interpreter and a URL router, the active guidelines interpreter and the URL router providing input to and monitoring output of the web browser, the active guidelines interpreter converting the active guidelines tags into a hyperlink for the web browser, the web browser displaying for the clinician the hyperlink associated with the clinical guideline; and
   c) when the clinician chooses a hyperlink presented by the web browser, the URL router receiving the active guideline tag associated with the chosen hyperlink and, if the chosen hyperlink is for an active guidelines order, sending a communication to the electronic medical records software system containing the stored order to cause an order to be entered.

10. The method of claim 9 wherein the sending of the communication to the electronic medical records software system includes sending the communication to an accumulator which accumulates communications for delivery to the electronic medical records software system.

11. In a computerized patient records system operated for a healthcare institution which maintains written clinical guidelines, a method of operating active guidelines comprising the steps of:
   a) on an active guidelines server, maintaining the clinical guidelines and also maintaining, associated with the clinical guidelines, active guideline tags containing information usable by the computerized patient records system to generate orders;
   b) at the station of a user, operating an active guidelines viewer in communication with the guidelines server, the active guidelines viewer including a web browser;
   c) an active guidelines interpreter;
   d) a URL router;
   i) the active guidelines interpreter receiving the active guidelines tags and converting the active guidelines tags into hyperlinks and passing the hyperlinks to the web browser,
   ii) the web browser receiving and displaying the hyperlink representing the active guidelines from the active guidelines interpreter for the user representing the active guideline; and
   e) when the user accepts a clinical guideline by invoking a hyperlink, the URL router receiving the active guideline tag associated with the invoked hyperlink and creating an action item from the active guideline tag to be sent to the computerized patient records system for implementation, the action item being processed by the computerized patient record system to create an order.

12. In a multiple server computer system to operate an electronic medical records software system and order entry in a healthcare institution, a method comprising the steps of
   a) providing an active guidelines server, the active guidelines server maintaining a set of clinical guidelines and a set of active guidelines tags, each of the active guidelines tags being associated with at least one of the clinical guidelines and including information usable by an electronic medical records system to generate orders;
   b) providing a workstation at the location of a clinician, the workstation operating an active guidelines viewer, the active guidelines viewer including a web browser;
   c) an active guidelines interpreter; and
   d) a URL router, the active guidelines interpreter and the URL router providing input to and monitoring output of the web browser, the active guidelines interpreter converting the active guidelines tags into a hyperlink for the web browser, the web browser displaying for the clinician the hyperlink associated with the clinical guideline; and
   e) when the clinician chooses a hyperlink presented by the web browser, the URL router receiving the active guideline tag associated with the chosen hyperlink and, if the chosen hyperlink is for an active guidelines order, sending a communication to the electronic medical records software system containing the stored order to cause an order to be entered.

* * * * *